(12) United States Patent
Hauptman et al.

(10) Patent No.: US 12,158,971 B2
(45) Date of Patent: Dec. 3, 2024

(54) DYNAMIC PATIENT HEALTH INFORMATION SHARING

(71) Applicant: Dexcom, Inc., San Diego, CA (US)

(72) Inventors: Alexis P. Hauptman, Portland, OR (US); James W. Barmettler, Portland, OR (US)

(73) Assignee: Dexcom, Inc., San Diego, CA (US)

( * ) Notice: Subject to any disclaimer, the term of this patent is extended or adjusted under 35 U.S.C. 154(b) by 84 days.

(21) Appl. No.: 17/815,308

(22) Filed: Jul. 27, 2022

(65) Prior Publication Data
US 2023/0046842 A1    Feb. 16, 2023

Related U.S. Application Data

(60) Provisional application No. 63/233,076, filed on Aug. 13, 2021.

(51) Int. Cl.
G06F 21/62 (2013.01)
G16H 10/60 (2018.01)

(52) U.S. Cl.
CPC ......... *G06F 21/6245* (2013.01); *G16H 10/60* (2018.01)

(58) Field of Classification Search
CPC ......... G16H 10/60; G16H 10/00–80/00; G06F 21/6245; G06F 1/00–2221/2153
See application file for complete search history.

(56) References Cited

U.S. PATENT DOCUMENTS

2008/0060059 A1\* 3/2008 Yoshida ............. H04L 63/0853
726/4
2010/0131298 A1   5/2010 Buttner et al.
(Continued)

FOREIGN PATENT DOCUMENTS

EP          2946323 A2 \* 11/2015   ......... G06F 19/3418

OTHER PUBLICATIONS

Daraghmi et al., "MedChain: A Design of Blockchain-Based System for Medical Records Access and Permissions Management," IEEE Access (vol. 7, 2019, pp. 164595-164613); DOI: 10.1109/ACCESS.2019.2952942. (Year: 2019).\*
(Continued)

*Primary Examiner* — Jonathon A. Szumny
(74) *Attorney, Agent, or Firm* — Patterson + Sheridan, LLP

(57) ABSTRACT

Certain aspects of the present disclosure relate to electronically sharing patient data. One aspect includes a method comprising capturing a computer readable code comprising an authentication code and clinic identifying information using an image capture component of a patient mobile device. The method also comprises authenticating the identified clinic with an information provider. The method further comprises displaying the clinic identifying information for confirmation and authenticating the patient. The method additionally comprises receiving a request to provide the clinic with patient data from the clinic. The method then comprises determining that the clinic is authorized to receive access to the patient data based on authentication of the clinic, authentication of the patient, and confirmation to share the patient data. The method also comprises transmitting the patient data to the clinic based on the determination that the clinic is authorized.

93 Claims, 5 Drawing Sheets

(56) References Cited

U.S. PATENT DOCUMENTS

| | | | | |
|---|---|---|---|---|
| 2015/0205919 A1* | 7/2015 | Robertson | ............... | G16H 10/60 |
| | | | | 705/3 |
| 2016/0117448 A1* | 4/2016 | Van De Craen | ....... | G16H 10/60 |
| | | | | 705/3 |
| 2018/0082050 A1* | 3/2018 | Flink | ..................... | H04L 9/3228 |
| 2018/0308566 A1* | 10/2018 | Dempers | ................ | G16H 10/60 |
| 2020/0388380 A1* | 12/2020 | Romanychev | ... | G06K 19/06037 |
| 2021/0304316 A1* | 9/2021 | Leddy, III | ........... | G06F 21/6245 |
| 2021/0313069 A1* | 10/2021 | Williams | ............... | G16H 50/30 |

OTHER PUBLICATIONS

Moudgil et al., "Cloud-based Secure Smartcard Healthcare Monitoring and Tracking System," 2017 Second International Conference on Electrical, Computer and Communication Technologies (ICECCT); DOI: 10.1109/ICECCT.2017.8117869. (Year: 2017).*
Rivero-Garcia et al., "Patients' Data Management System Protected by Identity-Based Authentication and Key Exchange," Sensors 2017, 17, 733; doi:10.3390/s17040733. (Year: 2017).*
International Search Report and Written Opinion for Application No. PCT/US2022/074283, mailed Nov. 9, 2022, 17 pages.
Wikipedia, "Authentication," Jul. 16, 2021, Retrieved from https://en.wikipedia.org/w/index.php?title=Authentication&oldid=1033898364, 12 pages.
Wikipedia, "QR code," Aug. 3, 2021, Retrieved from https://en.wikipedia.org/w/index.php?title=QR_code&oldid=1036853024, 35 pages.

* cited by examiner

DYNAMIC PATIENT HEALTH INFORMATION SHARING

CROSS-REFERENCE TO RELATED APPLICATIONS

This application claims priority to and benefit of U.S. Provisional Patent Application No. 63/233,076, filed Aug. 13, 2021, which is hereby assigned to the assignee hereof and hereby expressly incorporated by reference in its entirety as if fully set forth below and for all applicable purposes.

BACKGROUND

Field of the Disclosure

This application relates generally to sharing of electronic health data by a patient with a medical practitioner, a clinic, and the like.

Description of the Related Technology

Generally, data that is collected regarding a patient's health and medical condition ("health data") can help the patient and the medical practitioner monitor, manage, and treat the patient's health and condition. Often, the health data is generated and/or collected by the patient as well as various devices that the patient may use on a regular basis. As an example, the health data may comprise data regarding the patient's diet, exercise regimen, heart rate, analyte measurements, cholesterol measurements, and the like.

However, sharing of the health data with the medical practitioner can be resource consuming and problematic with respect to patient privacy and the like. For example, sharing physical records including the health data with the medical practitioner is inefficient and time-consuming both for the patient and the medical practitioner. In examples where the patient electronically shares records with a medical practitioner, existing methods and techniques for electronically sharing data may require that the patient manually identify the medical practitioner online before uploading the patient's health data to the identified medical practitioner. Therefore, existing methods and techniques for electronically sharing data can be inefficient and result in errors, such as sharing the wrong data, sharing the data with the wrong medical practitioner, and so forth.

This background is provided to introduce a brief context for the summary and detailed description that follow. This background is not intended to be an aid in determining the scope of the claimed subject matter nor be viewed as limiting the claimed subject matter to implementations that solve any or all of the disadvantages or problems presented above.

SUMMARY

Certain embodiments provide a method for securely sharing patient data. The method comprises capturing a computer readable code using an image capture component of a mobile device associated with a patient, the computer readable code comprising an authentication code provided to a healthcare clinic and clinic identifying information for the healthcare clinic. The method also comprises extracting the authentication code and the clinic identifying information from the computer readable code and authenticating the healthcare clinic with a health information provider based on the authentication code and the clinic identifying information. The method further comprises, upon authenticating the healthcare clinic with the health information provider, displaying the clinic identifying information to the patient via the mobile device for confirmation to share the patient data with the healthcare clinic and authenticating the patient based on matching patient authentication information with corresponding patient information stored by the mobile device or the health information provider. The method additionally comprises receiving a request from the healthcare clinic to provide the healthcare clinic with access to the patient data and determining that the healthcare clinic is authorized to receive access to the patient data based on authentication of the healthcare clinic, authentication of the patient, and the confirmation to share the patient data with the healthcare clinic from the patient. Furthermore, the method comprises transmitting the patient data, over a communication channel, to the healthcare clinic based on the determining that the healthcare clinic is authorized to receive access to the patient data.

In some embodiments, the computer readable code comprises one or more of a one-dimensional barcode, a two-dimensional barcode, a three-dimensional barcode, a logo, a graphic image, or an alphanumeric code and the image capture component comprises one of an image capture circuitry or a screen capture component of the mobile device. In some embodiments, the computer readable code is printed for display at the healthcare clinic, digitally displayed at the healthcare clinic, or digitally displayed on the mobile device. In some embodiments, extracting the authentication code comprises decrypting the authentication code and extracting the clinic identifying information comprises decrypting the clinic identifying information of the computer readable code based on the authentication code.

In some embodiments, authenticating the healthcare clinic comprises determining that the authentication code exists on a list of authenticated clinic codes and that the authentication code is associated with the clinic identifying information on the list of authenticated clinic codes. In some embodiments, authenticating the healthcare clinic further comprises providing the authentication code and the clinic identifying information to the health information provider and receiving acknowledgement that the authentication code and the clinic identifying information are associated on the list of authenticated clinic codes from the health information provider. In some embodiments, displaying the clinic identifying information further comprises prompting, via the mobile device, for confirmation that the displayed clinic identifying information matches the healthcare clinic with which the patient wants to share its information.

In some embodiments, the method further comprises obtaining the confirmation from the patient via the mobile device to share the patient data with the healthcare clinic and obtaining the patient authentication information from the mobile device to enable authentication of the patient before transmitting the patient data. In some embodiments, obtaining the patient authentication information comprises providing a prompt for the patient authentication information via the mobile device associated with the patient and receiving the patient authentication information in response to the provided prompt and the patient authentication information comprises personally identifiable information for the patient. In some embodiments, obtaining the patient authentication information comprises accessing the patient authentication information from a local application and the patient authentication information comprises personally identifiable information for the patient. In some embodiments, determining that the healthcare clinic is authorized to receive access to the patient data is further based on determining that the request is received from the healthcare clinic within a threshold time period of capturing the computer readable code.

In some embodiments, wherein extracting the authentication code and the clinic identifying information comprises parsing the computer readable code to identify a link to a webpage that includes one or more of a name, address information, or authentication code of the healthcare clinic and extracting the one or more of the name, the address information, or the authentication code from the webpage. In some embodiments, the method further comprises prompting the patient to input the patient authentication information, wherein the patient authentication information comprises one or more of a date of birth (DOB) or a name of the patient. In some embodiments, authenticating the patient comprises matching one or more of the DOB or the name of the patient with DOB and name information of the corresponding patient information. In some embodiments, the method further comprises determining whether the request from the healthcare clinic is received within a threshold period of capturing the computer readable code, wherein transmitting the patient data is further based on a determination that the request from the healthcare clinic is received within the threshold period of capturing the computer readable code.

In some embodiments, the method further comprises obtaining the threshold period from a configuration file. In some embodiments, the method further comprises determining that the request from the healthcare clinic is not received within a threshold period of capturing the computer readable code, displaying a first error message to the patient indicating that access to the patient data was not provided to the healthcare clinic based on the determination that the request from the healthcare clinic was not received within the threshold period, and transmitting a second error message to the healthcare clinic indicating that the request for the patient data from the healthcare clinic was not timely based on the determination that the request from the healthcare clinic was not received within the threshold period.

Certain other aspects provide a system for securely sharing patient data. The system comprises a memory storing instructions and a processor configured to execute the instructions. The processor is configured to execute the instructions to cause capturing a computer readable code using an image capture component of a mobile device associated with a patient, the computer readable code comprising an authentication code provided to a healthcare clinic and clinic identifying information for the healthcare clinic and extracting the authentication code and the clinic identifying information from the computer readable code. The processor is configured to execute the instructions to further cause authenticating the healthcare clinic with a health information provider based on the authentication code and the clinic identifying information and upon authenticating the healthcare clinic with the health information provider, displaying the clinic identifying information to the patient via the mobile device for confirmation to share the patient data with the healthcare clinic. The processor is configured to execute the instructions to also cause authenticating the patient based on matching patient authentication information with corresponding patient information stored by the mobile device or the health information provider and receiving a request from the healthcare clinic to provide the healthcare clinic with access to the patient data. The processor is configured to execute the instructions to additionally cause determining that the healthcare clinic is authorized to receive access to the patient data based on authentication of the healthcare clinic, authentication of the patient, and the confirmation to share the patient data with the healthcare clinic from the patient and transmitting the patient data, over a communication channel, to the healthcare clinic based on the determining that the healthcare clinic is authorized to receive access to the patient data.

Certain other aspects provide a non-transitory computer readable medium storing instructions, when executed by one or more processors, configured to perform a method for securely sharing patient data. The method comprises capturing a computer readable code using an image capture component of a mobile device associated with a patient, the computer readable code comprising an authentication code provided to a healthcare clinic and clinic identifying information for the healthcare clinic. The method also comprises extracting the authentication code and the clinic identifying information from the computer readable code and authenticating the healthcare clinic with a health information provider based on the authentication code and the clinic identifying information. The method further comprises upon authenticating the healthcare clinic with the health information provider, displaying the clinic identifying information to the patient via the mobile device for confirmation to share the patient data with the healthcare clinic and authenticating the patient based on matching patient authentication information with corresponding patient information stored by the mobile device or the health information provider. The method additionally comprises receiving a request from the healthcare clinic to provide the healthcare clinic with access to the patient data, determining that the healthcare clinic is authorized to receive access to the patient data based on authentication of the healthcare clinic, authentication of the patient, and the confirmation to share the patient data with the healthcare clinic from the patient, and transmitting the patient data, over a communication channel, to the healthcare clinic based on the determining that the healthcare clinic is authorized to receive access to the patient data.

BRIEF DESCRIPTION OF THE DRAWINGS

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
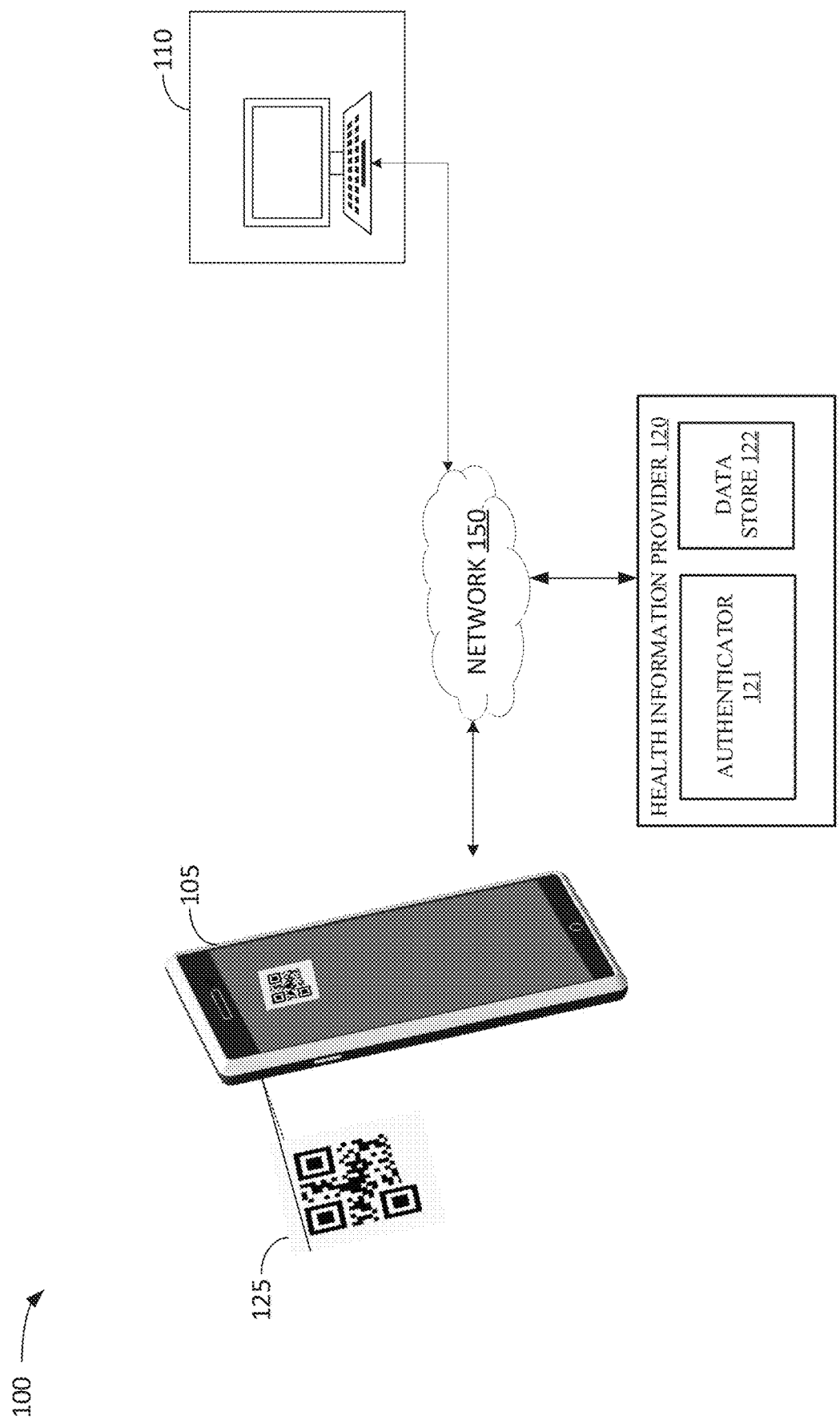
FIG. 1 illustrates a block diagram of an example health data system that enables a patient using a patient computing device to share health data with a clinic computing device of a clinic, according to some embodiments disclosed herein.

As discussed above, health data may be generated and collected by a patient over time. When diagnosing and treating a patient, a medical practitioner may gain insight from reviewing the health data shared by the patient. However, as described above, the sharing of the health data with the medical practitioner, however, may pose various technical challenges, such as efficiency of sharing the health data and privacy and security of the shared health data, described below. As used herein, the terms clinic and medical practitioner may be used interchangeably with reference to entities being authenticated and authorized to access a patient's health data. A medical practitioner may be associated with one or more clinics.

Examples of health data may include (1) data that the patient manually inputs (e.g., exercise data and nutrition information) into an electronic device (e.g., smart phone or computing device) and/or (2) data that is collected automatically (e.g., heart rate measurements, blood glucose measurements, activity data, and so forth) by an electronic device, such as a smart phone, various sensors (e.g., blood glucose meter, heart rate sensor, accelerometer, etc.), medicine administration devices (e.g., insulin pump), and so forth.

In certain examples, health software applications (hereinafter "applications") assist with tracking and storing the patient's health data. For example, a variety of applications may be used by Type 1 or Type 2 diabetic patients to monitor and store other aspects of the patients' diabetes. Numerous other applications exist for other medical conditions and may be similarly used. These applications can include intervention applications for supporting the treatment of the respective conditions and applications that help improve a patient's general health, such as activity tracking applications, dieting applications, and the like.

The patient may use one or more of these applications to monitor their health and/or any conditions they have, which involves health data being generated and stored for the patient. Where the patient suffers from diabetes, such health data may include, for example, glucose measurements collected by the blood glucose meter (e.g., continuous glucose monitor) over time, insulin dosages dispensed by an insulin pump, patient nutrition information based on what the patient consumes, general health data (for example, temperature, heart rate, general feeling, and similar data), activity data, and the like. In some instances, the application stores the health data locally, for example, on a same device that operates the application, such as a patient's mobile phone or other computing device. Alternatively, or additionally, the application may store the health data remotely, for example, in a cloud-based data store, e.g., with other patients' data. In some embodiments, the application is hosted or operated by or on behalf of a health information provider that manages and maintains the storage of the patient's health data.

Whether stored locally or remotely, the patient's health data may be private to the patient. Therefore, the patient may have to provide the clinic with physical copies of the patient's health data, manually enter the patient's health data into a data entry interface for the clinic, manually identify the clinic via an electronic interface for sharing the data electronically, or the like. However, efficiencies may be reduced when the patient manually obtains and shares the health data via hardcopies with the clinic, which would then have to manually enter the health data from the hardcopies. This manual process not only introduces errors but also takes time for both the patient and the clinic, especially where the volume of health data is extensive, which reduces efficiency of the sharing of the health data. The manual sharing of hardcopies of the patient data may also introduce privacy and/or security concerns where the hardcopies can be misplaced and disclose the patient data. Additionally, privacy and security concerns may arise where the patient manually shares the health data electronically through an electronic interface. For example, the patient can erroneously enter identifying information for the clinic to access the electronic interface, which may create issues of privacy and/or security with respect to the patient's health data if shared with the wrong clinic.

The deficiencies, issues, and concerns involved with sharing health data may actually deter the sharing of the patient's health data and may hamper on-boarding of the patient with a clinic.

Accordingly, the systems, methods, and apparatuses described herein provide technical solutions to the technical challenges associated with sharing of electronic health data, as described above. For example, certain aspects described herein enable the patient to more efficiently, securely, and privately share the patient's health data with a clinic. In some embodiments, the aspects involve the clinic providing the patient with a computer readable code that enables the patient to automatically and electronically share the patient's health data with the clinic.

Note that, although much of the description and examples below are described in relation to diabetes and similar conditions, the systems, methods, and apparatuses of the aspects described herein may be used in conjunction with any health-related application that the patient uses to monitor and store health data and with which the patient may authorize the clinic to access the health data in preparation for a visit at the clinic.

EXAMPLE SYSTEM

FIG. 1 illustrates a block diagram of an example health data system 100 that enables a patient using a patient computing device 105 (hereinafter referred to as "patient device 105") to share health data with a clinic computing device 110 (hereinafter referred to as "clinic device 110") of a clinic based on capturing a computer readable code 125 with the patient device 105, according to some embodiments disclosed herein. Capturing the computer readable code 125, which is specific to the clinic, enables the patient to determine whether to share the patient's health data, e.g., stored in a network accessible health information provider 120, with the clinic, as described in more detail below.

A network 150 communicatively couples the components of the system 100, such as the patient device 105 and the clinic device 110. Furthermore, the network 150 communicatively couples each of the patient device 105 and the clinic device 110 to the health information provider 120, including authenticator 121 and data store 122. In some embodiments, though not shown, the network 150 may communicatively couple additional patient devices 105 for the same or other patients and/or couple additional clinic devices 110 for the same or different clinics in the system 100. The network 150 may be a local area network (LAN), a wide area network (WAN), an intranet, the Internet, or any other type of network for connecting the patient device 105, the clinic device 110, the health information provider 120, etc.

The health information provider 120 stores health data in the data store 122 for one or more patients, including the patient using the patient device 105. The data store 122 may be remote from but accessible to each patient device 105 and clinic device 110 of the system 100. In some embodiments, the data store 122 stores health data in association with corresponding patient profiles. For example, each patient for which the data store 122 stores health data has a patient profile that links the health data to a unique patient identifier or other patient authenticating or identifying information, such as name, date of birth, Social Security number, contact information, patient identifier, and the like. In some embodiments, the patient profiles also store information regarding the patient(s), caregiver(s), and/or clinic(s) (collectively referred to as "entities" herein) that are authorized to access the respective patient's health data. In some embodiments, an entity that requests access to health data may have its own profile stored in the data store 122 that includes entity identifying information for the entity (such as contact information, an authentication code, a unique identifier, or the like) and information or a list regarding patients for whom the entity is authorized to access respective health data. In some embodiments, the patient profiles and/or the entity profiles can be stored in a separate authentication data store (not shown).

The health information provider 120 further comprises the authenticator 121 that authenticates whether an entity is able to access the health data stored in the data store 122 for a patient. The authenticator 121 may comprise a computing module, program, or the like configured to authenticate the entity requesting access to health data stored in the data store 122. For example, the health information provider 120 receives a request from a clinic to access the health data for an identified patient. The request may comprise an identifier for the clinic and patient identifying information introduced above for the patient whose health data is being requested.

Based on the clinic identifier and the patient identifying information, the authenticator 121 may determine whether the clinic is authorized to access the patient's health data stored in the data store 122. When authorizing an entity to access the patient's health data, the patient may use the patient device 105 to provide entity identifying information regarding the entity. For example, the patient may provide an element (for example, a piece, such as the name, address, etc.) of the entity identifying information for the entity to show that the entity is the correct entity to which the patient wants to provide access to the patient's health data. Further details regarding authorizing access to the patient's health data are provided below with respect to FIG. 2.

Though not shown explicitly in FIG. 1, the patient device 105 provides a user interface (UI) that enables the patient to interface with applications running on the patient device 105. The UI may enable the patient to run an application provided by or associated with the health information provider 120. The patient may use the application to manage (view, edit, or append) the patient's health data stored locally or in the data store 122. The UI may also enable the patient to confirm their identity and/or identities of entities requesting access to the patient's health data, for example, when confirming authorization of an entity to access the patient's health data.

The patient device 105 further comprises a scanning or image capture circuitry (also not shown in FIG. 1) that electronically captures the computer readable code 125. In some embodiments, the computer readable code 125 comprises one or more of a one-dimensional barcode, a two-dimensional barcode, a three-dimensional barcode, a logo, a graphic image, an encoded image, an alphanumeric code, and the like. The computer readable code 125 may be unique to a particular clinic and comprise identifying information for the clinic, such as name, address, phone number, and other contact information. In some embodiments, the computer readable code 125 also includes an authentication code. In certain embodiments, the computer readable code includes a link to a webpage at which the clinic identifying information can be obtained. In such embodiments, the patient device 105 is configured to extract the clinic identifying information from the webpage. In some embodiments, the authentication code can be assigned to a particular clinic or set of particular clinics that are authenticated as a legitimate clinic, for example, having one or more medical practitioners that are authenticated or registered with the health information provider 120.

The authentication code may be assigned by the health information provider to reduce opportunities for illegitimate clinics to access health data which they are not authorized to access. In some embodiments, the health information provider 120 may change or rotate authentication codes periodically. In some embodiments, the authentication code includes a hashing of particular data associated with the clinic and/or the health information provider 120 to ensure authenticity of the computer readable code. In some embodiments, the authentication code helps maintain Health Insurance Portability and Accountability Act (HIPAA) compliance by maintaining privacy and security constructs while sharing the health data.

The patient device 105 may also comprise a processor configured to parse the captured computer readable code to identify clinic information embedded within the computer readable code 125. The embedded clinic information comprises, for example, identifying information for the clinic, such as a name, phone number, and/or address of the clinic, and the like. Furthermore, in some embodiments, the processor is configured to parse the captured computer readable code to identify the authentication code for the identified clinic. As described in further detail below, the processor may further execute code stored in a memory of the patient device 105 to perform one or more additional functions described herein, such as in relation to FIG. 2.

The clinic device 110 may be used by the medical practitioner at the clinic to access health data, for example, for a patient in advance of or during a scheduled visit, to monitor the patient's health and medical condition between visits, and the like. In some embodiments, the clinic device 110 may obtain the health data directly from the patient, for example, via the patient device 105 or access the health data from the data store 122. The clinic device 110 may comprise one or more of a personal computer, a mobile computing device, a server, and the like. In some embodiments, the clinic device 110 is configured to perform various operations, as described in more detail below. For example, the clinic device 110 can print, generate, display computer readable code 125 and provide a user interface that allows a user at the clinic to add address info and an authentication code that uniquely identifies the clinic to health information provider 120.

Figure 2:
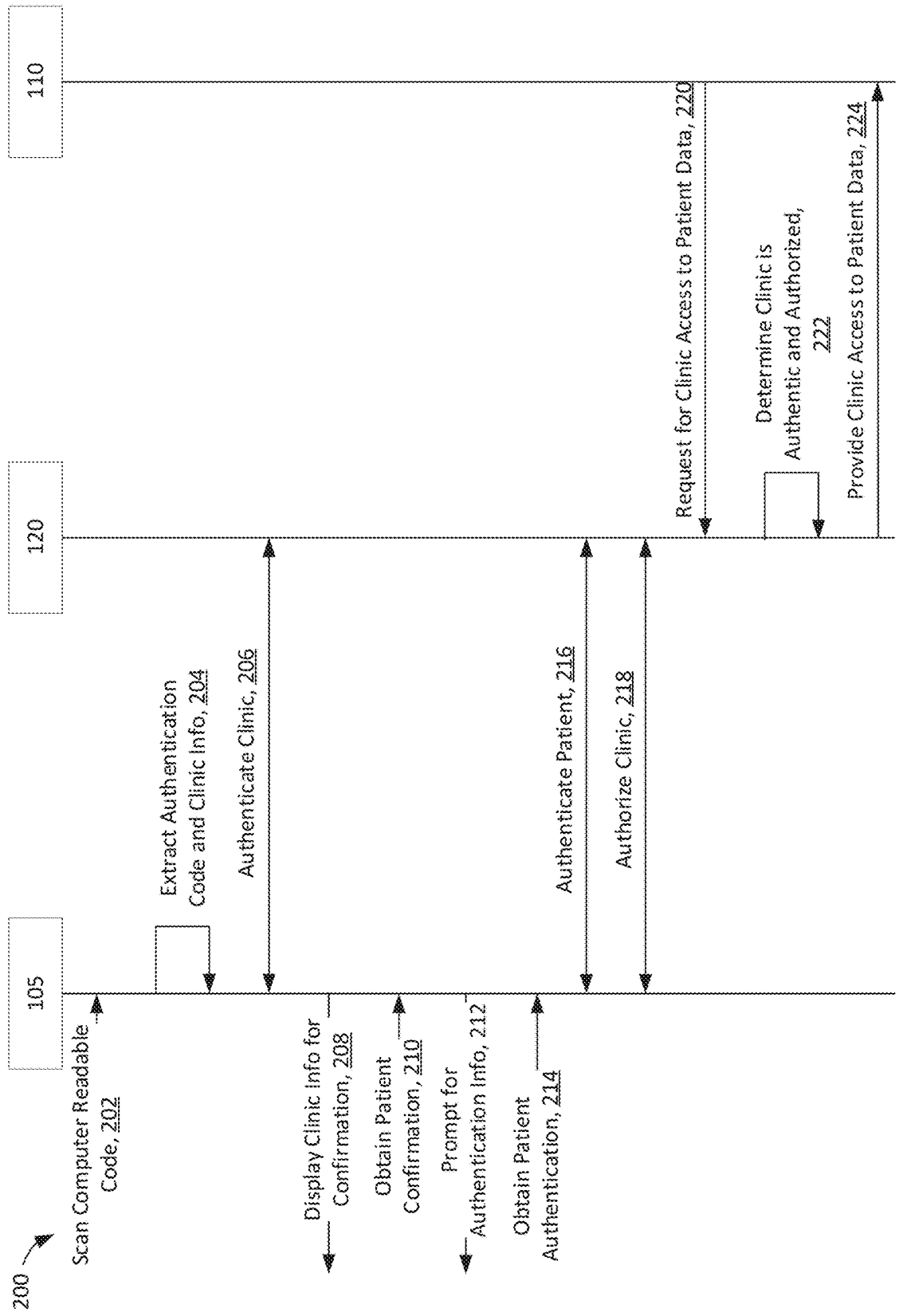
FIG. 2 illustrates a sequence diagram illustrating communications exchanged between or processing performed by components of the health data system of FIG. 1, according to some embodiments described herein.

FIG. 2 illustrates a sequence diagram 200 illustrating communications exchanged between or processing performed by components of the system 100 of FIG. 1 to enable sharing of patient data with the clinic device 110 based on capturing the computer readable code 125 with the patient device 105, according to some embodiments described herein. While the sequence diagram 200 and corresponding description include reference to components of the system 100 of FIG. 1, the steps of the sequence diagram 200 are not limited to that example embodiment and may apply to various other combinations of components in various other use cases. Furthermore, the sequence diagram 200 is not required to perform each of or only the indicated steps and is not limited to performing the indicated steps in any particular order.

The sequence diagram 200 depicts interactions between the patient device 105, the health information provider 120, and the clinic device 110. The sequence diagram 200 begins at step 202 with a patient using the patient device 105 to capture a computer readable code, which corresponds to the computer readable code 125. The computer readable code may be associated with a specific clinic, for example, that is requesting access to the patient's health data.

The patient operating the patient device 105 may access the computer readable code in various ways. For example, the computer readable code may be displayed to the patient when the patient is at a clinic scheduling an appointment or when the patient checks-in or arrives for the appointment. The computer readable code provided in the clinic may be displayed on a print out or digitally displayed via a monitor or other electronic screen at the clinic. In some embodiments, the computer readable code is provided via an e-mail, text message, or other physical or electronic communication to the patient. The patient may capture the computer readable code using the patient device 105, for example, via the scanning or image capture circuitry or a screen capture component of patient device 105. For example, when the computer readable code is displayed on the clinic monitor or printed, the patient may capture the computer readable code with the scanning or image capture circuitry. In another example, when the computer readable code is displayed on a display of the patient device 105, the patient may capture the computer readable code via the screen capture component and corresponding processing.

At processing step 204, the patient device 105 processes the captured computer readable code and extracts data therefrom. In some embodiments, the patient device 105 processes the captured computer readable code to extract clinic identifying information associated with the clinic, such as name and address information, or the like. In some embodiments, the patient device 105 further identifies the authentication code from the captured computer readable code. In some embodiments, processing the captured computer readable code comprises decrypting encrypted data that is extracted from the computer readable code, such as the authentication code and/or clinic identifying information. In some embodiments, the authentication code, once extracted, can be used to decrypt at least a portion of the clinic identifying information.

At communication step 206, the patient device 105 and the health information provider 120 exchange communications and information to authenticate the clinic identified in the computer readable code. For example, the patient device 105 may communicate the authentication code to the health information provider 120. The authenticator 121 (shown in FIG. 1) of the health information provider 120 may access the data store 122 (shown in FIG. 1) to identify name and contact information for the specific clinic. The identified name and contact information for the clinic may be communicated back to the patient device 105 for patient confirmation of the clinic. Alternatively, or additionally, the patient device 105 communicates both the authentication code and the clinic identifying information extracted from the computer readable code to the health information provider 120. In such examples, the health information provider 120, via the authenticator 121, may then compare the clinic identifying information extracted from the computer readable code to the clinic name and contact information that is mapped in the data store 122 to the authentication code. The authentication code may be compared to a list of authentication codes maintained by the health information provider and associated with the corresponding clinic identifying information. If the clinic cannot be authenticated, the communication from the health information provider 120 may return an error indicating such to the patient device 105 and terminate further communications until the clinic is authenticated at communication step 206. If the clinic is authenticated, then the health information 120 may return confirmation or acknowledgement that the clinic is authenticated based on the authentication code and clinic identifying information. In some embodiments, aspects of the communication step 206 may be optional, for example, when the computer readable code does not include the authentication code to decrypt and authenticate.

At communication step 208, the patient device 105 displays the clinic identifying information extracted from the computer readable code to the patient for confirmation by the patient. For example, when the patient scans a barcode to enable sharing of the patient's health data with a clinic, the patient device 105 can display the name of the clinic, as extracted from the barcode, on the display of the patient device 105 via the UI. In some embodiments, patient device 105 further displays contact information for the clinic, as extracted from the computer readable code or retrieved from the data store 122, and a prompt to the patient to confirm that the patient wants to authorize the identified clinic to access the patient's health data. For example, when the patient scans the computer readable code at an ABC clinic, the patient device 105 may extract the ABC clinic's name and contact information from the computer readable code for display to and confirmation by the patient.

In some embodiments, the prompt may provide the patient with options to confirm access to the ABC clinic, deny access to the ABC clinic, or provide access to the ABC clinic with limits, such as a duration, a number of accesses, and the like. In some embodiments, when the patient denies access to the ABC clinic, the patient device 105 may prompt the patient for a reason why the patient is denying access, such as the wrong clinic is identified. In some embodiments, when the patient device 105 extracts the name "XYZ clinic" (instead of ABC clinic) from the computer readable code displayed in the ABC clinic, the patient device 105 determines that the computer readable code is fraudulent or erroneous based on the patient's denial of access to the ABC clinic and an indication that the wrong clinic is identified. Such determination may be communicated to the health information provider 120 (not shown) with a flag indicating a potential fraudulent or erroneous computer readable code. Thus, the patient device 105 and the health information provider 120 may determine when there is an error with respect to the computer readable code or a bad actor (e.g., a fraudulent clinic).

At communication step 210, the patient device 105 obtains confirmation from the patient of intent to share the patient's health data with the clinic identified in the computer readable code. Where the confirmation includes any limits on the sharing (for example, frequency or duration limits), the patient device 105 may note such limitations and provide such limitations to the health information provider 120. In some embodiments, the patient also uses the patient device 105 to update entity authorizations to access the patient's health data. For example, the patient can remove authorization for an entity when that entity no longer works with the patient. In some embodiments, the patient can authorize the entity to access the health data a specified number of times or for a specified period. Such authorizations may be stored as part of the patient's and/or entity's profile.

At optional communication step 212, the patient device 105 prompts the patient to authenticate themselves. In some embodiments, the prompt may request specific information, such as date of birth, patient identifier, Social Security number, and the like. This authentication step ensures that the person providing authorization for the clinic to access the patient's health data is in fact the patient and not someone else having access to the patient device 105.

At optional communication step 214, the patient provides the requested information for confirmation of the identity of the patient. In some embodiments, the requested information is personally identifiable information.

In some embodiments, communications steps 212 and 214 may be optional or performed automatically by the application that is, e.g., provided by health information provider 120 and executed on the patient device 105. For example, if the patient scans the computer readable code while the application is executing on the patient device 105, the application may obtain patient authentication information from the patient's login information for the application in order to authenticate the patient with the health information provider 120. Thus, if the patient is logged into the application and scans the computer readable code at communication step 202, the application may bypass prompting the patient for and obtaining patient authentication information at the communication steps 212 and 214 and instead provide patient authentication information based on the patient having logged into the application.

At communication steps 216, the patient device 105 and the health information provider 120 authenticate the patient based on the authentication information received via communication step 214 or via the application. Specifically, the health information provider 120, via the authenticator 121, may use the authentication information for the patient to confirm that it is in fact the patient (or someone that has access to the patient's authentication information) that is using the patient device 105. For example, the authenticator 121 may confirm that the patient authentication information (for example, the date of birth, and so forth) matches with corresponding patient identifying information stored in the patient's profile in the data store 122. Where the health information provider 120 confirms that the authentication information and the patient identifying information match, the health information provider 120 determines that the patient (or someone that has access to the patient's authentication information) is operating the patient device 105 and allows for further communication. Where the health information provider 120 determines that the authentication information and the patient identifying information do not match, the health information provider 120 determines that the patient is not operating the patient device 105.

Where the health information provider 120 determines that the patient is not operating the patient device 105, the health information provider 120 does not allow the patient device 105 to authorize access to the patient's health data and may terminate communications. Thus, further communications may be denied until the patient is able to be authenticated at communication step 216.

At communication step 218, the patient device 105 and the health information provider 120 authorize the clinic to access the patient's health data based on authenticating the patient at communication step 216 and receiving confirmation from the patient that the clinic is the clinic that the patient wants to be provided access to the patient's health data. In some embodiments, the authorization to provide the clinic with access to the patient's health data may be provisional, dependent on a request from the clinic to access the patient's health data within a threshold amount of time, and so forth, as described herein. If any of the authentication of the patient at communication step 216, the authentication of the clinic at communication step 206, or the confirmation by the patient at communication steps 208 and 210 are not successful, the clinic is not authorized to access this patient's health data.

At communication step 220, the health information provider 120 receives a request from the clinic device 110 to obtain access to the patient's health data. In some embodiments, the request for access to the patient's health data includes patient identifying information (or an aspect thereof, such as name, patient identifier number, Social Security number, and the like) for the patient whose health data the clinic is requesting and an identifier of the clinic.

At processing step 222, the health information provider 120 may determine whether the clinic is authorized to access the health data for the patient identified in the request of communication step 220. In response to the request at step 220, the health information provider 120 (for example, via the authenticator 121) may authenticate the clinic identified in the request to ensure that the clinic is authorized to access the patient's health data. Authenticating the clinic may comprise verifying that the clinic requesting access to the patient's data is the clinic that is identified in the request and not another entity posing as the clinic. For example, the authentication may include verifying that the request includes clinic identifying information that should be known only by the requesting clinic, such as the authentication code with a corresponding clinic profile.

In some embodiments, health information provider 120 provides authorization to access the health data for the identified patient if the patient identified in the request of the communication step 220 has authorized the clinic to access the patient's health data. If the patient has authorized access to the patient's health data for the requesting clinic (for example, as determined based on the communication step 218), the health information provider 120 may grant access to the patient's health data at 224 for the requesting clinic.

In some embodiments, the health information provider 120 determines, as an additional check, whether the request from the clinic for access to the patient's health data was received within a threshold time of the patient authorizing access to the patient's health data for the clinic at communication step 218. This determination may act as an additional authentication step at processing step 222. For example, the clinic may request access to the patient's health data after an appointment is scheduled or once the patient checks in for the appointment. As such, where the computer readable code is available for capture after the patient checks in for an appointment, the health information provider 120 may determine whether the clinic request for the health data was received within a threshold time of, for example, two hours of the patient authorizing access for the clinic. Alternatively, if the patient was provided the computer readable code via e-mail or other messaging (electronic or physical) accessible by the patient when not at the clinic, then the threshold time may be a number of days or weeks between the clinic request and the patient authorizing access. In some embodiments, such verification of receipt of the request from the clinic within the threshold time of the patient capturing the computer readable code and authorizing the clinic to access the patient's health data can operate as a check against providing access to health data for unauthorized clinics. In some embodiments, the threshold time may be defined by a configuration file of the health information provider or for the clinic.

In some embodiments, the request from the clinic may comprise patient information and clinic identifying information. The health information provider 120 may compare the clinic's request (requesting access to the patient health data) with the patient's request (to provide access to the clinic). Where the corresponding data matches, the health information provider 120 provides the clinic with access to the patient's health data without further analysis or authentication.

At communication step 224, the health information provider 120 provides the clinic device 110 access to the health data per the request received at communication step 220 when authenticated and authorized. In some embodiments, though not shown in FIG. 2, when the health information provider 120 determines, at processing 222, that the clinic is not authorized to access the health data, the health information provider 120 may provide a communication to the clinic denying access to the requested health data. Such denial may include a reason for the denial (for example, the request at communication step 220 was received outside the threshold window of the encoded image being scanned at communication step 202 or the clinic was not authorized to access the patient's health data at 218). In some embodiments, when the clinic is not authorized to access health data, the health information provider 120 may provide a flag or other indicator to the patient device 105 for the patient whose health data was requested. Such information may enable the clinic and/or the patient to troubleshoot the denial of access to the patient's health data.

Figure 3:
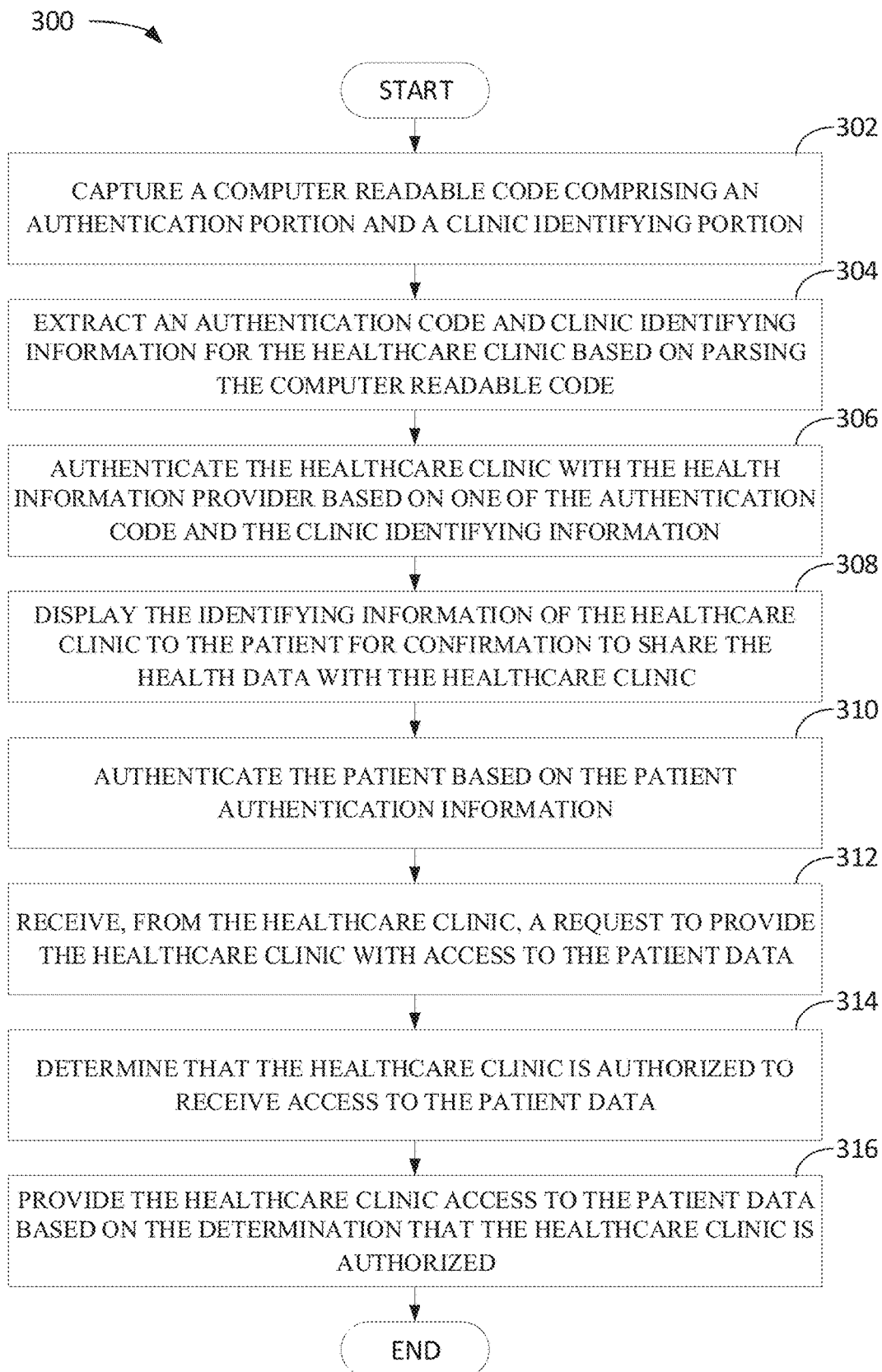
FIG. 3 depicts example operations for sharing of patient data with the clinic computing device of FIG. 1, according to some embodiments described herein.

FIG. 3 depicts example operations 300 for sharing of patient data with a clinic device based on capturing the computer readable code with a patient device, according to some embodiments described herein. For example, operations 300 may be performed by one or more components of the system 100 FIG. 1, such as the patient device 105, the health information provider 120, and/or the clinic device 110.

At block 302, a computer readable code, comprising an authentication code and clinic identifying information, is captured, for example, by a scanning or image capture circuitry or a screen capture component of the patient device 105. Further details associated with operations of block 302 were described in relation to step 202 of FIG. 2.

At block 304, an authentication code and clinic identifying information for the healthcare clinic is extracted based on parsing the computer readable code by the processor of the patient device 105. Further details associated with operations of block 304 were described in relation to step 204 of FIG. 2.

At block 306, the healthcare clinic is authenticated with the health information provider 120 based on one or more of the authentication code and the clinic identifying information. Further details associated with operations of block 306 were previously described in relation to step 206 of FIG. 2.

At block 308, the clinic identifying information of the clinic is displayed to the patient on the patient device 105 for confirmation to authenticate the clinic and authorize the clinic to access the patient's health data via the patient device 105. Further details associated with operations of block 308 were previously described in relation to steps 208 and 210 of FIG. 2.

At block 310, the patient is authenticated based on one or more of patient authentication information received from the patient via the patient device 105 or via the application operating on the patient device 105. Further details associated with operations of block 310 were previously described in relation to steps 212 and 214 of FIG. 2.

At block 312, a request is received from the clinic to provide the clinic with access to the health data for the patient. The request may be received by the health information provider 120. Further details associated with operations of block 312 were previously described in relation to step 216 of FIG. 2.

At block 314, the clinic is determined to be authorized to receive access to the patient data. For example, the health information provider 120 may determine that the clinic is authorized to access the patient data. Further details associated with operations of block 314 were previously described in relation to steps 218 and 222 of FIG. 2.

At block 316, the clinic is provided access to the health data based on the determination that the clinic is authorized. For example, the healthcare information provider 120 provides the clinic with access to the health data. Further details associated with operations of block 316 were previously described in relation to step 224 of FIG. 2.

Figure 4:
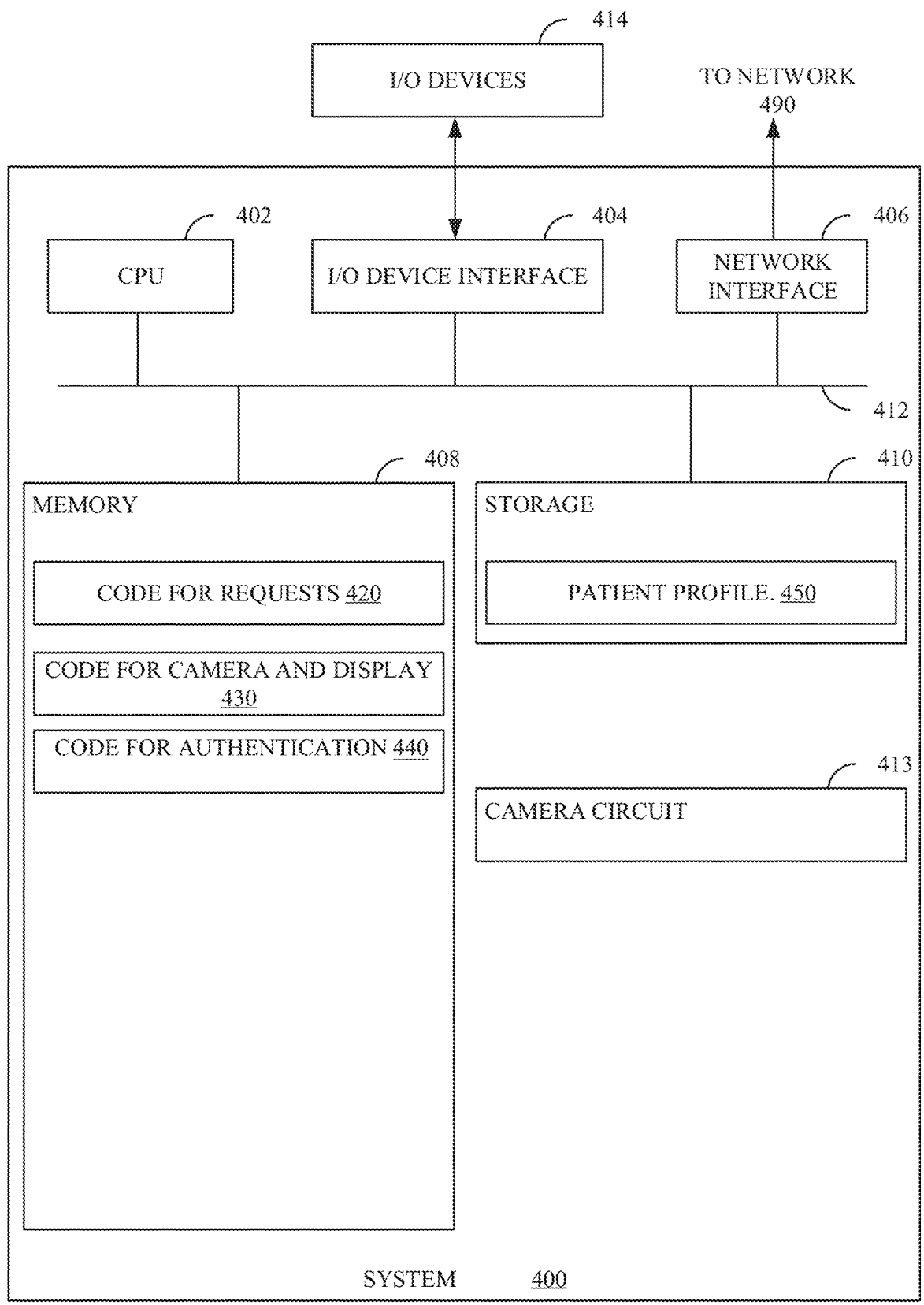
FIG. 4 is a diagram of an embodiment of a processing system that performs or embodies certain aspects described herein.

FIG. 4 is a diagram of an embodiment of a processing system 400 that performs or embodies certain aspects described herein. For example, system 400 may correspond to the patient device 105 illustrated in FIGS. 1 and 2.

As shown, system 400 includes a central processing unit (CPU) 402, one or more I/O device interfaces 404 that may allow for the connection of various I/O devices 414 (e.g., keyboards, displays, mouse devices, pen input, etc.) to the system 400, network interface 406 through which system 400 is connected to network 490 (which may correspond to the network 150), a memory 408, a storage 410, an interconnect 412, and a camera circuit 413 (which may correspond to the scanning or image capture circuitry introduced above).

CPU 402 may retrieve and execute programming instructions stored in the memory 408. Similarly, the CPU 402 may retrieve and store application data residing in the memory 408. The interconnect 412 transmits programming instructions and application data, among the CPU 402, I/O device interface 404, network interface 406, memory 408, storage 410, and camera circuit 413.

CPU 402 is included to be representative of a single CPU, multiple CPUs, a single CPU having multiple processing cores, and the like.

Memory 408 is representative of a volatile memory, such as a random access memory, and/or a nonvolatile memory, such as nonvolatile random access memory, phase change random access memory, or the like. As shown, memory 408 includes code for camera and display 430, code for authentication 440, and code for requests 420.

The code for managing information requests 420 generally manages requests for information (such as confirmation of information, providing of information, and the like) received, for example, via the network 150 (such as from the health information provider 120) or an application executed by the system 400. In some embodiments, the code for managing information requests 420 enables handling of requests for confirmation or prompts for information, as described, for example, with respect to steps 208, 210, 212, and 214 of FIG. 2.

The code for the camera circuitry and display 430 generally enables the camera circuit 413 to capture a computer readable code comprising the authentication code and the clinic identifying information, as further described in relation to step 202 of FIG. 2. In some embodiments, the code for camera circuit and display 430 enables screen capture capabilities of the patient device 105 that enables the patient to capture the computer readable code displayed on the display of the patient device 105. In some embodiments, the code for camera circuit and display 430 enables the extraction of the authentication code and clinic identifying information for the clinic based on parsing the computer readable code and display of various information, prompts, and requests, as described with respect to steps 204, 208, and 212 of FIG. 2. The code for authentication generally enables CPU 402 to perform any of the authentication steps performed by patient device 105 in relation to steps 206, 214, 216, and 218 of FIG. 2.

The storage 410 stores various data, such as the patient profile 450 (corresponding to the patient profiles and patient health data introduced above) for the patient using the system 400, which may be locally stored in some embodiments.

The camera circuit 413 corresponds to any scanning or image capture circuitry that enables capture of an image displayed externally from or on a display of a device, such as the patient device 105.

Figure 5:
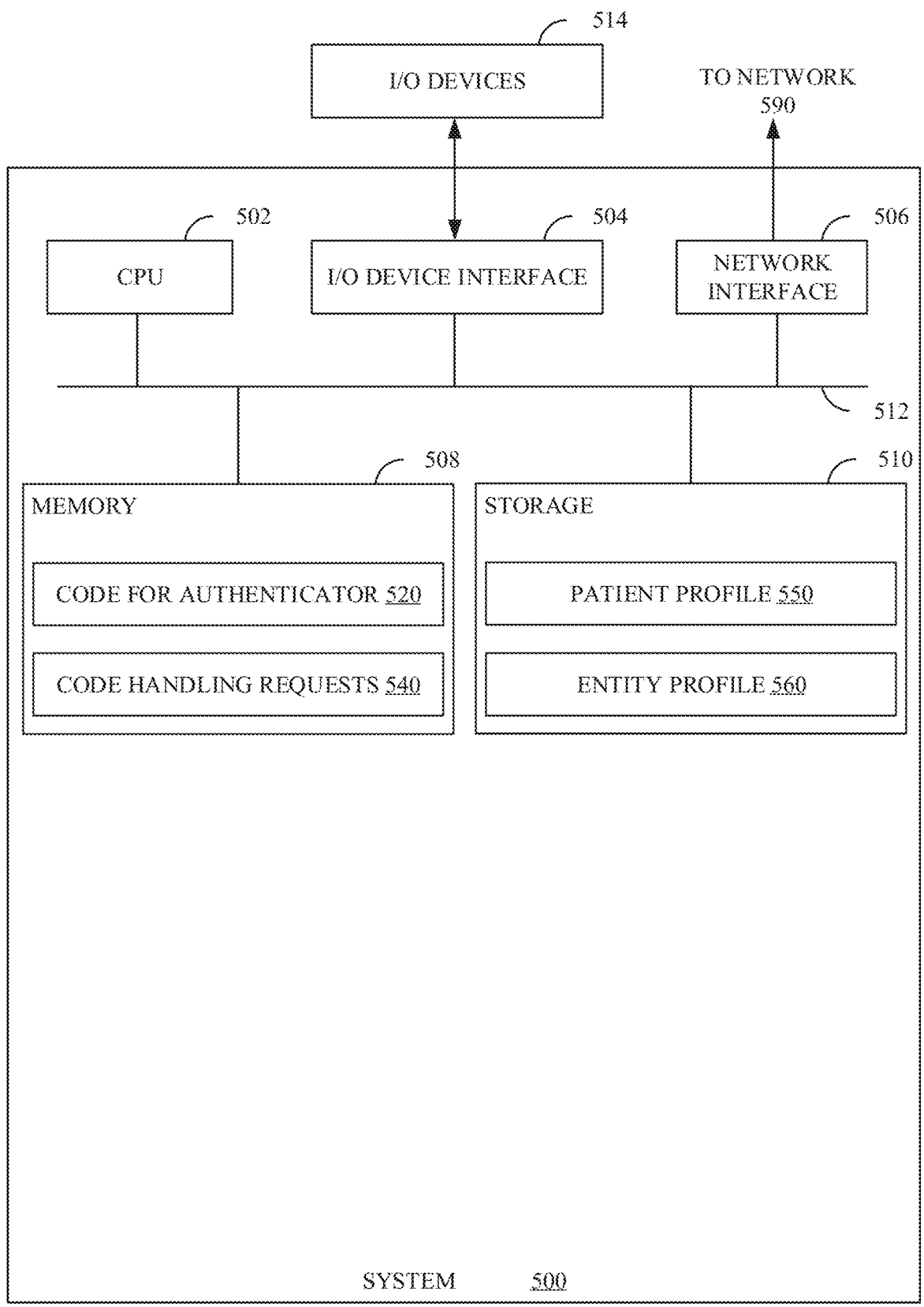
FIG. 5 is a diagram of an embodiment of a processing system that performs or embodies certain aspects described herein.

FIG. 5 is a diagram of an embodiment of a processing system 500 that performs or embodies certain aspects described herein. For example, system 500 may correspond to health information provider 120 illustrated in FIGS. 1 and 2.

As shown, system 500 includes a central processing unit (CPU) 502, one or more I/O device interfaces 504 that may allow for the connection of various I/O devices 514 (e.g., keyboards, displays, mouse devices, pen input, etc.) to the system 500, network interface 506 through which system 500 is connected to network 590 (which may correspond to the network 150), a memory 508, a storage 510, and an interconnect 512.

CPU 502 may retrieve and execute programming instructions stored in the memory 508. Similarly, the CPU 502 may retrieve and store application data residing in the memory 508. The interconnect 512 transmits programming instructions and application data, among the CPU 502, I/O device interface 504, network interface 506, memory 508, and storage 510.

CPU 502 is included to be representative of a single CPU, multiple CPUs, a single CPU having multiple processing cores, and the like.

Memory 508 is representative of a volatile memory, such as a random access memory, and/or a nonvolatile memory, such as nonvolatile random access memory, phase change random access memory, or the like. As shown, memory 508 includes code for an authenticator (for example, the authenticator 121) 520 and code for handling requests 540.

The code for the authenticator 520 generally authenticates the clinic based on one of an authentication code and clinic identifying information, authenticates the patient based on the patient authentication information, and determines that the clinic is authorized to receive access to the health data. In some embodiments, the code for the authenticator 520 enables clinic authentication as described with respect to step 206, enables patient authentication as described with respect to step 216, authorizes the clinic as described with respect to step 218, and determines that the clinic is authenticated and authorized as described with respect to steps 222 of FIG. 2.

The code for handling information requests 540 generally enables the health information provider 120 to receive and respond to requests, such as a request to authenticate a patient, authenticate a clinic, or authorize a clinic. In some embodiments, the code for handling requests 540 enables the health information provider 120 to receive, from the clinic, a request to provide the clinic with access to the health data based on the determination that the clinic is authorized to access the health data for a patient. In some embodiments, the code for handling requests 540 enables the health information provider 120 to receive, from the patient device 105, a request to authenticate the patient. In some embodiments, the code for handling requests 540 enables the provision of access to client data for a requesting clinic, as described with respect to steps 220, 222, and 224 of FIG. 2, among others.

The storage 510 stores various data, such as patient profiles 550 (corresponding to the patient profiles and patient health data introduced above) and entity profiles 560 (corresponding to the entity profiles introduced above).

Each of these non-limiting examples can stand on its own or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method for securely sharing patient data, comprising:
   capturing a computer-readable code using an image capture component of a mobile device associated with a patient, the computer-readable code comprising an authentication code provided to a healthcare clinic and clinic identifying information for the healthcare clinic;
   extracting the authentication code and the clinic identifying information from the computer-readable code, wherein:
      the authentication code is extracted by decrypting the authentication code, and
      the clinic identifying information is extracted by decrypting the clinic identifying information of the computer-readable code based on the authentication code;
   authenticating the healthcare clinic with a health information provider based on the authentication code and the clinic identifying information;
   upon authenticating the healthcare clinic with the health information provider, displaying the clinic identifying information to the patient via the mobile device for confirmation to share the patient data with the healthcare clinic;
   authenticating the patient based on matching patient authentication information with corresponding patient information stored by the mobile device or the health information provider;
   receiving a request from the healthcare clinic to provide the healthcare clinic with access to the patient data;
   determining that the healthcare clinic is authorized to receive access to the patient data based on authentication of the healthcare clinic, authentication of the patient, and the confirmation to share the patient data with the healthcare clinic from the patient; and
   transmitting the patient data, over a communication channel, to the healthcare clinic based on determining that the healthcare clinic is authorized to receive access to the patient data.

2. The method of claim 1, wherein:
   the computer-readable code comprises one or more of a one-dimensional barcode, a two-dimensional barcode, a three-dimensional barcode, a logo, a graphic image, or an alphanumeric code, and
   the image capture component comprises one of an image capture circuitry or a screen capture component of the mobile device.

3. The method of claim 1, wherein the computer-readable code is printed for display at the healthcare clinic, digitally displayed at the healthcare clinic, or digitally displayed on the mobile device.

4. The method of claim 1, wherein authenticating the healthcare clinic comprises determining that the authentication code exists on a list of authenticated clinic codes and that the authentication code is associated with the clinic identifying information on the list of authenticated clinic codes.

5. The method of claim 4, wherein authenticating the healthcare clinic further comprises providing the authentication code and the clinic identifying information to the health information provider and receiving acknowledgement that the authentication code and the clinic identifying information are associated on the list of authenticated clinic codes from the health information provider.

6. The method of claim 1, wherein displaying the clinic identifying information further comprises prompting, via the mobile device, for confirmation that the displayed clinic identifying information matches the healthcare clinic with which the patient wants to share its information.

7. The method of claim 1, further comprising:
   obtaining the confirmation from the patient via the mobile device to share the patient data with the healthcare clinic; and
   obtaining the patient authentication information from the mobile device to enable authentication of the patient before transmitting the patient data.

8. The method of claim 7, wherein:
   obtaining the patient authentication information comprises providing a prompt for the patient authentication information via the mobile device associated with the patient and receiving the patient authentication information in response to the provided prompt, and
   the patient authentication information comprises personally identifiable information for the patient.

9. The method of claim 7, wherein:
   obtaining the patient authentication information comprises accessing the patient authentication information from a local application, and
   the patient authentication information comprises personally identifiable information for the patient.

10. The method of claim 1, wherein determining that the healthcare clinic is authorized to receive access to the patient data is further based on determining that the request is received from the healthcare clinic within a threshold time period of capturing the computer-readable code.

11. The method of claim 1, wherein extracting the authentication code and the clinic identifying information comprises:

parsing the computer-readable code to identify a link to a webpage that includes one or more of a name, address information, or authentication code of the healthcare clinic; and extracting the one or more of the name, the address information, or the authentication code from the webpage.

12. The method of claim 1, further comprising prompting the patient to input the patient authentication information, wherein the patient authentication information comprises one or more of a date of birth (DOB) or a name of the patient.

13. The method of claim 12, wherein authenticating the patient comprises matching one or more of the DOB or the name of the patient with DOB and name information of the corresponding patient information.

14. The method of claim 1, further comprising determining whether the request from the healthcare clinic is received within a threshold period of capturing the computer-readable code, wherein transmitting the patient data is further based on a determination that the request from the healthcare clinic is received within the threshold period of capturing the computer-readable code.

15. The method of claim 14, further comprising obtaining the threshold period from a configuration file.

16. The method of claim 1, further comprising:
determining that an initial request from the healthcare clinic is not received within a threshold period of capturing the computer-readable code;
displaying a first error message to the patient indicating that access to the patient data was not provided to the healthcare clinic based on the determination that the initial request from the healthcare clinic was not received within the threshold period; and
transmitting a second error message to the healthcare clinic indicating that the initial request for the patient data from the healthcare clinic was not timely based on the determination that the initial request from the healthcare clinic was not received within the threshold period.

17. A system for securely sharing patient data, comprising:
at least one memory storing instructions; and
at least one processor configured to execute the instructions to:
capture a computer-readable code using an image capture component of a mobile device associated with a patient, the computer-readable code comprising an authentication code provided to a healthcare clinic and clinic identifying information for the healthcare clinic;
extract the authentication code from the computer-readable code by decrypting the authentication code;
extract the clinic identifying information from the computer-readable code by decrypting the clinic identifying information based on the authentication code;
authenticate the healthcare clinic with a health information provider based on the authentication code and the clinic identifying information;
upon authenticating the healthcare clinic with the health information provider, display the clinic identifying information to the patient via the mobile device for confirmation to share the patient data with the healthcare clinic;
authenticate the patient based on matching patient authentication information with corresponding patient information stored by the mobile device or the health information provider;
receive a request from the healthcare clinic to provide the healthcare clinic with access to the patient data;
determine that the healthcare clinic is authorized to receive access to the patient data based on authentication of the healthcare clinic, authentication of the patient, and the confirmation to share the patient data with the healthcare clinic from the patient; and
transmit the patient data, over a communication channel, to the healthcare clinic based on determining that the healthcare clinic is authorized to receive access to the patient data.

18. A non-transitory computer-readable storage medium storing instructions, that when executed by one or more processors, cause the one or more processors to perform a method for securely sharing patient data, the method comprising:
capturing a computer-readable code using an image capture component of a mobile device associated with a patient, the computer-readable code comprising an authentication code provided to a healthcare clinic and clinic identifying information for the healthcare clinic;
extracting the authentication code and the clinic identifying information from the computer-readable code, wherein:
the authentication code is extracted by decrypting the authentication code, and
the clinic identifying information is extracted by decrypting the clinic identifying information based on the authentication code;
authenticating the healthcare clinic with a health information provider based on the authentication code and the clinic identifying information;
upon authenticating the healthcare clinic with the health information provider, displaying the clinic identifying information to the patient via the mobile device for confirmation to share the patient data with the healthcare clinic;
authenticating the patient based on matching patient authentication information with corresponding patient information stored by the mobile device or the health information provider;
receiving a request from the healthcare clinic to provide the healthcare clinic with access to the patient data;
determining that the healthcare clinic is authorized to receive access to the patient data based on authentication of the healthcare clinic, authentication of the patient, and the confirmation to share the patient data with the healthcare clinic from the patient; and
transmitting the patient data, over a communication channel, to the healthcare clinic based on determining that the healthcare clinic is authorized to receive access to the patient data.

19. The system of claim 17, wherein:
the computer-readable code comprises one or more of a one-dimensional barcode, a two-dimensional barcode, a three-dimensional barcode, a logo, a graphic image, or an alphanumeric code, and
the image capture component comprises one of an image capture circuitry or a screen capture component of the mobile device.

20. The system of claim 17, wherein the computer-readable code is printed for display at the healthcare clinic, digitally displayed at the healthcare clinic, or digitally displayed on the mobile device.

21. The system of claim 17, wherein the authentication of the healthcare clinic comprises determining that the authentication code exists on a list of authenticated clinic codes and that the authentication code is associated with the clinic identifying information on the list of authenticated clinic codes.

22. The system of claim 21, wherein the authentication of the healthcare clinic further comprises providing the authentication code and the clinic identifying information to the health information provider and receiving acknowledgement that the authentication code and the clinic identifying information are associated on the list of authenticated clinic codes from the health information provider.

23. The system of claim 17, wherein the display of the clinic identifying information further comprises prompting, via the mobile device, for confirmation that the displayed clinic identifying information matches the healthcare clinic with which the patient wants to share its information.

24. The system of claim 17, wherein the processor is further configured to execute the instructions to:
obtain confirmation from the patient via the mobile device to share the patient data with the healthcare clinic; and
obtain patient authentication information from the mobile device to enable authentication of the patient before transmitting the patient data.

25. The system of claim 24, wherein:
obtaining the patient authentication information comprises providing a prompt for the patient authentication information via the mobile device associated with the patient and receiving the patient authentication information in response to the provided prompt, and
the patient authentication information comprises personally identifiable information for the patient.

26. The system of claim 24, wherein:
obtaining the patient authentication information comprises accessing the patient authentication information from a local application, and
the patient authentication information comprises personally identifiable information for the patient.

27. The system of claim 17, wherein the determination that the healthcare clinic is authorized to receive access to the patient data is further based on a determination that the request is received from the healthcare clinic within a threshold time period of capturing the computer-readable code.

28. The system of claim 17, wherein the extraction of the authentication code and the clinic identifying information comprises:
parsing the computer-readable code to identify a link to a webpage that includes one or more of a name, address information, or authentication code of the healthcare clinic; and
extracting the one or more of the name, the address information, or the authentication code from the webpage.

29. The system of claim 17, wherein the processor is further configured to execute the instructions to prompt the patient to input the patient authentication information, wherein the patient authentication information comprises one or more of a date of birth (DOB) or a name of the patient.

30. The system of claim 29, wherein the authentication of the patient comprises matching one or more of the DOB or the name of the patient with DOB and name information of the corresponding patient information.

31. The system of claim 17, wherein the processor is further configured to execute the instructions to:
determine whether the request from the healthcare clinic is received within a threshold period of capturing the computer-readable code, wherein the transmission of the patient data is further based on a determination that the request from the healthcare clinic is received within the threshold period of capturing the computer-readable code.

32. The system of claim 31, wherein the processor is further configured to execute the instructions to obtain the threshold period from a configuration file.

33. The system of claim 17, wherein the processor is further configured to execute the instructions to:
determine that an initial request from the healthcare clinic is not received within a threshold period of capturing the computer-readable code;
display a first error message to the patient indicating that access to the patient data was not provided to the healthcare clinic based on the determination that the initial request from the healthcare clinic was not received within the threshold period; and
transmit a second error message to the healthcare clinic indicating that the initial request for the patient data from the healthcare clinic was not timely based on the determination that the initial request from the healthcare clinic was not received within the threshold period.

34. The non-transitory computer-readable storage medium of claim 18, wherein:
the computer-readable code comprises one or more of a one-dimensional barcode, a two-dimensional barcode, a three-dimensional barcode, a logo, a graphic image, or an alphanumeric code, and
the image capture component comprises one of an image capture circuitry or a screen capture component of the mobile device.

35. The non-transitory computer-readable storage medium of claim 18, wherein the computer-readable code is printed for display at the healthcare clinic, digitally displayed at the healthcare clinic, or digitally displayed on the mobile device.

36. The non-transitory computer-readable storage medium of claim 18, wherein authenticating the healthcare clinic comprises determining that the authentication code exists on a list of authenticated clinic codes and that the authentication code is associated with the clinic identifying information on the list of authenticated clinic codes.

37. The non-transitory computer-readable storage medium of claim 36, wherein authenticating the healthcare clinic further comprises providing the authentication code and the clinic identifying information to the health information provider and receiving acknowledgement that the authentication code and the clinic identifying information are associated on the list of authenticated clinic codes from the health information provider.

38. The non-transitory computer-readable storage medium of claim 18, wherein displaying the clinic identifying information further comprises prompting, via the mobile device, for confirmation that the displayed clinic identifying information matches the healthcare clinic with which the patient wants to share its information.

39. The non-transitory computer-readable storage medium of claim 18, wherein the method further comprises:
obtaining the confirmation from the patient via the mobile device to share the patient data with the healthcare clinic; and obtaining the patient authentication information from the mobile device to enable authentication of the patient before transmitting the patient data.

40. The non-transitory computer-readable storage medium of claim 39, wherein:
   obtaining the patient authentication information comprises providing a prompt for the patient authentication information via the mobile device associated with the patient and receiving the patient authentication information in response to the provided prompt, and
   the patient authentication information comprises personally identifiable information for the patient.

41. The non-transitory computer-readable storage medium of claim 39, wherein:
   obtaining the patient authentication information comprises accessing the patient authentication information from a local application, and
   the patient authentication information comprises personally identifiable information for the patient.

42. The non-transitory computer-readable storage medium of claim 18, wherein determining that the healthcare clinic is authorized to receive access to the patient data is further based on determining that the request is received from the healthcare clinic within a threshold time period of capturing the computer-readable code.

43. The non-transitory computer-readable storage medium of claim 18, wherein extracting the authentication code and the clinic identifying information comprises:
   parsing the computer-readable code to identify a link to a webpage that includes one or more of a name, address information, or authentication code of the healthcare clinic; and
   extracting the one or more of the name, the address information, or the authentication code from the webpage.

44. The non-transitory computer-readable storage medium of claim 18, wherein the method further comprises prompting the patient to input the patient authentication information, wherein the patient authentication information comprises one or more of a date of birth (DOB) or a name of the patient.

45. The non-transitory computer-readable storage medium of claim 44, wherein authenticating the patient comprises matching one or more of the DOB or the name of the patient with DOB and name information of the corresponding patient information.

46. The non-transitory computer-readable storage medium of claim 18, wherein the method further comprises determining whether the request from the healthcare clinic is received within a threshold period of capturing the computer-readable code, wherein transmitting the patient data is further based on a determination that the request from the healthcare clinic is received within the threshold period of capturing the computer-readable code.

47. The non-transitory computer-readable storage medium of claim 46, wherein the method further comprises obtaining the threshold period from a configuration file.

48. The non-transitory computer-readable storage medium of claim 18, wherein the method further comprises:
   determining that an initial request from the healthcare clinic is not received within a threshold period of capturing the computer-readable code;
   displaying a first error message to the patient indicating that access to the patient data was not provided to the healthcare clinic based on the determination that the initial request from the healthcare clinic was not received within the threshold period; and
   transmitting a second error message to the healthcare clinic indicating that the initial request for the patient data from the healthcare clinic was not timely based on the determination that the initial request from the healthcare clinic was not received within the threshold period.

49. A method for securely sharing patient data, comprising:
   capturing a computer-readable code using an image capture component of a mobile device associated with a patient, the computer-readable code comprising an authentication code provided to a healthcare clinic and clinic identifying information for the healthcare clinic;
   extracting the authentication code and the clinic identifying information from the computer-readable code;
   authenticating the healthcare clinic with a health information provider based on the authentication code and the clinic identifying information by:
      determining that the authentication code exists on a list of authenticated clinic codes and that the authentication code is associated with the clinic identifying information on the list of authenticated clinic codes,
      providing the authentication code and the clinic identifying information to the health information provider, and
      receiving acknowledgement that the authentication code and the clinic identifying information are associated on the list of authenticated clinic codes from the health information provider;
   upon authenticating the healthcare clinic with the health information provider, displaying the clinic identifying information to the patient via the mobile device for confirmation to share the patient data with the healthcare clinic;
   authenticating the patient based on matching patient authentication information with corresponding patient information stored by the mobile device or the health information provider;
   receiving a request from the healthcare clinic to provide the healthcare clinic with access to the patient data;
   determining that the healthcare clinic is authorized to receive access to the patient data based on authentication of the healthcare clinic, authentication of the patient, and the confirmation to share the patient data with the healthcare clinic from the patient; and
   transmitting the patient data, over a communication channel, to the healthcare clinic based on determining that the healthcare clinic is authorized to receive access to the patient data.

50. The method of claim 49, wherein:
   the computer-readable code comprises one or more of a one-dimensional barcode, a two-dimensional barcode, a three-dimensional barcode, a logo, a graphic image, or an alphanumeric code, and
   the image capture component comprises one of an image capture circuitry or a screen capture component of the mobile device.

51. The method of claim 49, wherein the computer-readable code is printed for display at the healthcare clinic, digitally displayed at the healthcare clinic, or digitally displayed on the mobile device.

52. The method of claim 49, wherein:
   extracting the authentication code comprises decrypting the authentication code, and extracting the clinic identifying information comprises decrypting the clinic identifying information of the computer-readable code based on the authentication code.

53. The method of claim 49, wherein displaying the clinic identifying information further comprises prompting, via the mobile device, for confirmation that the displayed clinic identifying information matches the healthcare clinic with which the patient wants to share its information.

54. The method of claim 49, further comprising:
obtaining the confirmation from the patient via the mobile device to share the patient data with the healthcare clinic; and
obtaining the patient authentication information from the mobile device to enable authentication of the patient before transmitting the patient data.

55. The method of claim 54, wherein:
obtaining the patient authentication information comprises providing a prompt for the patient authentication information via the mobile device associated with the patient and receiving the patient authentication information in response to the provided prompt, and
the patient authentication information comprises personally identifiable information for the patient.

56. The method of claim 54, wherein:
obtaining the patient authentication information comprises accessing the patient authentication information from a local application, and
the patient authentication information comprises personally identifiable information for the patient.

57. The method of claim 49, wherein determining that the healthcare clinic is authorized to receive access to the patient data is further based on determining that the request is received from the healthcare clinic within a threshold time period of capturing the computer-readable code.

58. The method of claim 49, wherein extracting the authentication code and the clinic identifying information comprises:
parsing the computer-readable code to identify a link to a webpage that includes one or more of a name, address information, or authentication code of the healthcare clinic; and
extracting the one or more of the name, the address information, or the authentication code from the webpage.

59. The method of claim 49, further comprising prompting the patient to input the patient authentication information, wherein the patient authentication information comprises one or more of a date of birth (DOB) or a name of the patient.

60. The method of claim 59, wherein authenticating the patient comprises matching one or more of the DOB or the name of the patient with DOB and name information of the corresponding patient information.

61. The method of claim 49, further comprising determining whether the request from the healthcare clinic is received within a threshold period of capturing the computer-readable code, wherein transmitting the patient data is further based on a determination that the request from the healthcare clinic is received within the threshold period of capturing the computer-readable code.

62. The method of claim 61, further comprising obtaining the threshold period from a configuration file.

63. The method of claim 49, further comprising:
determining that an initial request from the healthcare clinic is not received within a threshold period of capturing the computer-readable code;
displaying a first error message to the patient indicating that access to the patient data was not provided to the healthcare clinic based on the determination that the initial request from the healthcare clinic was not received within the threshold period; and
transmitting a second error message to the healthcare clinic indicating that the initial request for the patient data from the healthcare clinic was not timely based on the determination that the initial request from the healthcare clinic was not received within the threshold period.

64. A system for securely sharing patient data, comprising:
at least one memory storing instructions; and
at least one processor configured to execute the instructions to:
capture a computer-readable code using an image capture component of a mobile device associated with a patient, the computer-readable code comprising an authentication code provided to a healthcare clinic and clinic identifying information for the healthcare clinic;
extract the authentication code and the clinic identifying information from the computer-readable code;
authenticate the healthcare clinic with a health information provider based on the authentication code and the clinic identifying information, wherein the authentication further comprises determining that the authentication code exists on a list of authenticated clinic codes and that the authentication code is associated with the clinic identifying information on the list of authenticated clinic codes, providing the authentication code and the clinic identifying information to the health information provider, and receiving acknowledgement that the authentication code and the clinic identifying information are associated on the list of authenticated clinic codes from the health information provider;
upon authenticating the healthcare clinic with the health information provider, display the clinic identifying information to the patient via the mobile device for confirmation to share the patient data with the healthcare clinic;
authenticate the patient based on matching patient authentication information with corresponding patient information stored by the mobile device or the health information provider;
receive a request from the healthcare clinic to provide the healthcare clinic with access to the patient data;
determine that the healthcare clinic is authorized to receive access to the patient data based on authentication of the healthcare clinic, authentication of the patient, and the confirmation to share the patient data with the healthcare clinic from the patient; and
transmit the patient data, over a communication channel, to the healthcare clinic based on determining that the healthcare clinic is authorized to receive access to the patient data.

65. The system of claim 64, wherein:
the computer-readable code comprises one or more of a one-dimensional barcode, a two-dimensional barcode, a three-dimensional barcode, a logo, a graphic image, or an alphanumeric code, and
the image capture component comprises one of an image capture circuitry or a screen capture component of the mobile device.

66. The system of claim 64, wherein the computer-readable code is printed for display at the healthcare clinic, digitally displayed at the healthcare clinic, or digitally displayed on the mobile device.

67. The system of claim 64, wherein:
extracting the authentication code comprises decrypting the authentication code, and
extracting the clinic identifying information comprises decrypting the clinic identifying information of the computer-readable code based on the authentication code.

68. The system of claim 64, wherein the display of the clinic identifying information further comprises prompting, via the mobile device, for confirmation that the displayed clinic identifying information matches the healthcare clinic with which the patient wants to share its information.

69. The system of claim 64, wherein the processor is further configured to execute the instructions to:
obtain confirmation from the patient via the mobile device to share the patient data with the healthcare clinic; and
obtain patient authentication information from the mobile device to enable authentication of the patient before transmitting the patient data.

70. The system of claim 69, wherein:
obtaining the patient authentication information comprises providing a prompt for the patient authentication information via the mobile device associated with the patient and receiving the patient authentication information in response to the provided prompt, and
the patient authentication information comprises personally identifiable information for the patient.

71. The system of claim 69, wherein:
obtaining the patient authentication information comprises accessing the patient authentication information from a local application, and
the patient authentication information comprises personally identifiable information for the patient.

72. The system of claim 64, wherein the determination that the healthcare clinic is authorized to receive access to the patient data is further based on a determination that the request is received from the healthcare clinic within a threshold time period of capturing the computer-readable code.

73. The system of claim 64, wherein the extraction of the authentication code and the clinic identifying information comprises:
parsing the computer-readable code to identify a link to a webpage that includes one or more of a name, address information, or authentication code of the healthcare clinic; and
extracting the one or more of the name, the address information, or the authentication code from the webpage.

74. The system of claim 64, wherein the processor is further configured to execute the instructions to prompt the patient to input the patient authentication information, wherein the patient authentication information comprises one or more of a date of birth (DOB) or a name of the patient.

75. The system of claim 74, wherein the authentication of the patient comprises matching one or more of the DOB or the name of the patient with DOB and name information of the corresponding patient information.

76. The system of claim 64, wherein the processor is further configured to execute the instructions to:
determine whether the request from the healthcare clinic is received within a threshold period of capturing the computer-readable code, wherein the transmission of the patient data is further based on a determination that the request from the healthcare clinic is received within the threshold period of capturing the computer-readable code.

77. The system of claim 76, wherein the processor is further configured to execute the instructions to obtain the threshold period from a configuration file.

78. The system of claim 64, wherein the processor is further configured to execute the instructions to:
determine that an initial request from the healthcare clinic is not received within a threshold period of capturing the computer-readable code;
display a first error message to the patient indicating that access to the patient data was not provided to the healthcare clinic based on the determination that the initial request from the healthcare clinic was not received within the threshold period; and
transmit a second error message to the healthcare clinic indicating that the initial request for the patient data from the healthcare clinic was not timely based on the determination that the initial request from the healthcare clinic was not received within the threshold period.

79. A non-transitory computer-readable storage medium storing instructions, that when executed by one or more processors, cause the one or more processors to perform a method for securely sharing patient data, the method comprising:
capturing a computer-readable code using an image capture component of a mobile device associated with a patient, the computer-readable code comprising an authentication code provided to a healthcare clinic and clinic identifying information for the healthcare clinic;
extracting the authentication code and the clinic identifying information from the computer-readable code;
authenticating the healthcare clinic with a health information provider based on the authentication code and the clinic identifying information by determining that the authentication code exists on a list of authenticated clinic codes and that the authentication code is associated with the clinic identifying information on the list of authenticated clinic codes, providing the authentication code and the clinic identifying information to the health information provider, and receiving acknowledgement that the authentication code and the clinic identifying information are associated on the list of authenticated clinic codes from the health information provider;
upon authenticating the healthcare clinic with the health information provider, displaying the clinic identifying information to the patient via the mobile device for confirmation to share the patient data with the healthcare clinic;
authenticating the patient based on matching patient authentication information with corresponding patient information stored by the mobile device or the health information provider;
receiving a request from the healthcare clinic to provide the healthcare clinic with access to the patient data;
determining that the healthcare clinic is authorized to receive access to the patient data based on authentication of the healthcare clinic, authentication of the patient, and the confirmation to share the patient data with the healthcare clinic from the patient; and transmitting the patient data, over a communication channel, to the healthcare clinic based on determining that the healthcare clinic is authorized to receive access to the patient data.

80. The non-transitory computer-readable storage medium of claim 79, wherein:
the computer-readable code comprises one or more of a one-dimensional barcode, a two-dimensional barcode, a three-dimensional barcode, a logo, a graphic image, or an alphanumeric code, and
the image capture component comprises one of an image capture circuitry or a screen capture component of the mobile device.

81. The non-transitory computer-readable storage medium of claim 79, wherein the computer-readable code is printed for display at the healthcare clinic, digitally displayed at the healthcare clinic, or digitally displayed on the mobile device.

82. The non-transitory computer-readable storage medium of claim 79, wherein:
extracting the authentication code comprises decrypting the authentication code, and
extracting the clinic identifying information comprises decrypting the clinic identifying information of the computer-readable code based on the authentication code.

83. The non-transitory computer-readable storage medium of claim 79, wherein displaying the clinic identifying information further comprises prompting, via the mobile device, for confirmation that the displayed clinic identifying information matches the healthcare clinic with which the patient wants to share its information.

84. The non-transitory computer-readable storage medium of claim 79, wherein the method further comprises:
obtaining the confirmation from the patient via the mobile device to share the patient data with the healthcare clinic; and
obtaining the patient authentication information from the mobile device to enable authentication of the patient before transmitting the patient data.

85. The non-transitory computer-readable storage medium of claim 84, wherein:
obtaining the patient authentication information comprises providing a prompt for the patient authentication information via the mobile device associated with the patient and receiving the patient authentication information in response to the provided prompt, and
the patient authentication information comprises personally identifiable information for the patient.

86. The non-transitory computer-readable storage medium of claim 84, wherein:
obtaining the patient authentication information comprises accessing the patient authentication information from a local application, and
the patient authentication information comprises personally identifiable information for the patient.

87. The non-transitory computer-readable storage medium of claim 79, wherein determining that the healthcare clinic is authorized to receive access to the patient data is further based on determining that the request is received from the healthcare clinic within a threshold time period of capturing the computer-readable code.

88. The non-transitory computer-readable storage medium of claim 79, wherein extracting the authentication code and the clinic identifying information comprises:
parsing the computer-readable code to identify a link to a webpage that includes one or more of a name, address information, or authentication code of the healthcare clinic; and
extracting the one or more of the name, the address information, or the authentication code from the webpage.

89. The non-transitory computer-readable storage medium of claim 79, wherein the method further comprises prompting the patient to input the patient authentication information, wherein the patient authentication information comprises one or more of a date of birth (DOB) or a name of the patient.

90. The non-transitory computer-readable storage medium of claim 89, wherein authenticating the patient comprises matching one or more of the DOB or the name of the patient with DOB and name information of the corresponding patient information.

91. The non-transitory computer-readable storage medium of claim 79, wherein the method further comprises determining whether the request from the healthcare clinic is received within a threshold period of capturing the computer-readable code, and wherein transmitting the patient data is further based on a determination that the request from the healthcare clinic is received within the threshold period of capturing the computer-readable code.

92. The non-transitory computer-readable storage medium of claim 91, wherein the method further comprises obtaining the threshold period from a configuration file.

93. The non-transitory computer-readable storage medium of claim 79, wherein the method further comprises:
determining that an initial request from the healthcare clinic is not received within a threshold period of capturing the computer-readable code;
displaying a first error message to the patient indicating that access to the patient data was not provided to the healthcare clinic based on the determination that the initial request from the healthcare clinic was not received within the threshold period; and
transmitting a second error message to the healthcare clinic indicating that the initial request for the patient data from the healthcare clinic was not timely based on the determination that the initial request from the healthcare clinic was not received within the threshold period.

* * * * *